United States Patent [19]

Gosline et al.

[11] 4,347,854

[45] Sep. 7, 1982

[54] BIPOLAR TEMPERATURE MEASURING APPARATUS

[76] Inventors: Scott P. Gosline, P.O. Box 41962, Atlanta, Ga. 30331; William F. Stembridge; James C. Sturrock, both of P.O. Box 90756, East Point, Ga. 30364

[21] Appl. No.: 85,118

[22] Filed: Oct. 15, 1979
(Under 37 CFR 1.47)

[51] Int. Cl.³ .............................................. A61B 5/00
[52] U.S. Cl. ..................................... 128/736; 374/166
[58] Field of Search ................................ 128/734–736; 73/351, 362 AR

[56] References Cited

U.S. PATENT DOCUMENTS

| | | | |
|---|---|---|---|
| 1,648,939 | 11/1927 | Evins | 128/736 |
| 2,947,171 | 8/1960 | Peltola | 73/351 |
| 3,520,187 | 7/1970 | Petersen | 128/736 |
| 3,651,694 | 3/1972 | Lamb | 128/736 |
| 3,933,149 | 1/1976 | Salera et al. | 128/736 |

*Primary Examiner*—Kyle L. Howell
*Assistant Examiner*—Francis J. Jaworski
*Attorney, Agent, or Firm*—Jones & Askew

[57] ABSTRACT

Apparatus for measuring and visually displaying skin temperature of a body, human or animal, at each of two bilateral locations along a linear path of travel. Two separate temperature probes provide analog temperature-responsive signals that are digitized to drive separate digital displays directly indicating the measured skin temperature at each bilateral location. A movement-responsive device provides signals corresponding to movement of the instrument along the longitudinal path, and those motion signals can be correlated with the sensed temperatures at bilaterally-spaced locations along that path.

10 Claims, 7 Drawing Figures

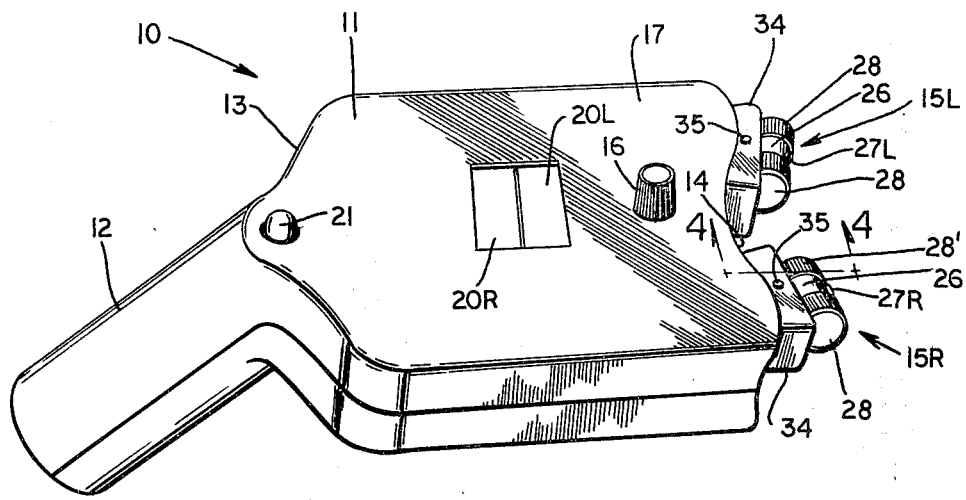
FIG_1
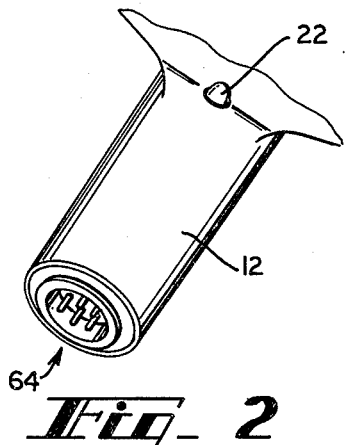
FIG_2
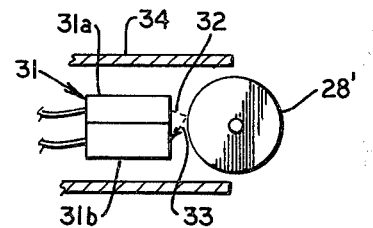
FIG_4
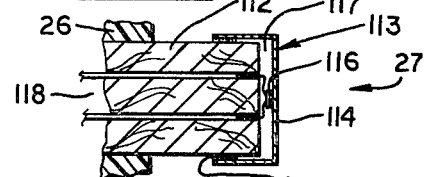
FIG_6
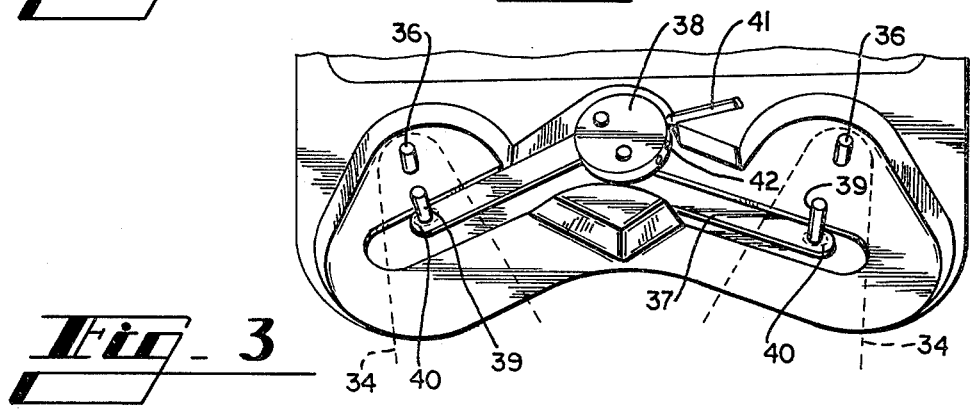
FIG_3

BIPOLAR TEMPERATURE MEASURING APPARATUS

BACKGROUND OF THE INVENTION

This invention relates in general to temperature measuring and indicating apparatus, and particular to apparatus for separately measuring and indicating the skin temperature at two points bilaterally disposed across the spinal column of a person.

Measuring the temperature at various body points of a living organism, whether human or animal, is a recognized technique for diagnosing the existence and possible nature of body malfunctions or ailments. The measurement of internal body temperature is one well-known diagnostic technique, and other known diagnostic techniques involved measuring the external or skin temperature at one or more locations on the body. In the practice of chiropractic, for example, the presence of a neural imbalance may be indicated by localized anomalies of the skin temperature in a known relation to the point of imbalance. If the chiropractor can detect the presence and location of a neural imbalance by measuring the resulting temperature anomaly, which may be in the order of a few tenths of a degree fahrenheit, he may then seek to correct the underlying cause of the neural imbalance by adjusting the spinal column of the patient.

With the knowledge that neural imbalances may be detected by measuring skin temperature adjacent the spinal column, diagnostic devices have been proposed in the prior art for measuring skin temperature in the vicinity of the spinal column. Such prior devices generally seek to obtain a measurement based on the skin temperature at two bilateral points, that is, two points lying on a line approximately perpendicular to the spinal column and spaced approximately equidistant from the spinal column. Such diagnostic temperature measuring devices of the prior art have generally been less than satisfactory, however, for a number of reasons. Some such devices measured only the presence of a temperature differential between the two bilateral locations, and thus failed to show either the actual skin temperature or the specific temperatures producing a bilateral temperature anomaly. Other problems associated with such skin temperature measuring instruments of the prior art have included an unacceptably slow reaction time, poor accuracy, and difficulty in locating for spinal adjustment the particular location along the spinal column at which the temperature anomaly was measured.

SUMMARY OF INVENTION

Accordingly, it is an object of the present invention to provide an improved temperature measuring apparatus for diagnostic or other purposes.

It is another object of the present invention to provide improved apparatus for measuring skin temperature of a living organism such as a human or animal body.

It is yet another object of the present invention to provide improved apparatus for bilateral measurement of skin temperature along the spinal column.

Stated in general terms, the present invention comprises a hand-held temperature measuring instrument having two separate temperature responsive probes with relatively low response time to skin temperature changes. The probes produce an electrical signal as a function of measured temperature. The electrical signal from each probe is supplied to a separate measurement and display channel, each of which drives a separate indicator such as a digital display to indicate the measured temperature directly in degrees for each temperature probe. The two temperature probes are mounted in the housing of the apparatus for bilateral positioning along the spinal column, and the position of each probe relative to the spinal column can be simultaneously adjusted to maintain proper bilateral measurement. The temperature probes are mounted in housings adapted to be traversed over the body, such as along a longitudinal path adjacent to the spinal column, and a distance signal is generated by the apparatus indicating the extent of such longitudinal movement along the spinal column.

The nature of the present invention, as well as other objects and advantages thereof, will become more readily apparent from the following description of a preferred embodiment.

BRIEF DESCRIPTION OF DRAWINGS

FIG. 1 is a pictorial view showing the exterior of a bilateral temperature indicating apparatus according to a disclosed embodiment of the present invention.

FIG. 2 is a partial pictorial view showing a portion of the underside of the apparatus shown in FIG. 1.

FIG. 3 is an internal view showing details of a mechanism for positioning the temperature sensing assemblies in the apparatus of FIG. 1.

FIG. 4 is a section view of a temperature sensing assembly in the apparatus of FIG. 1, showing a mechanism for measuring distance travelling along the skin surface.

FIG. 6 is a section view showing details of one of the temperature measuring probes used in the disclosed embodiment.

DESCRIPTION OF PREFERRED EMBODIMENT

Figure 5A:
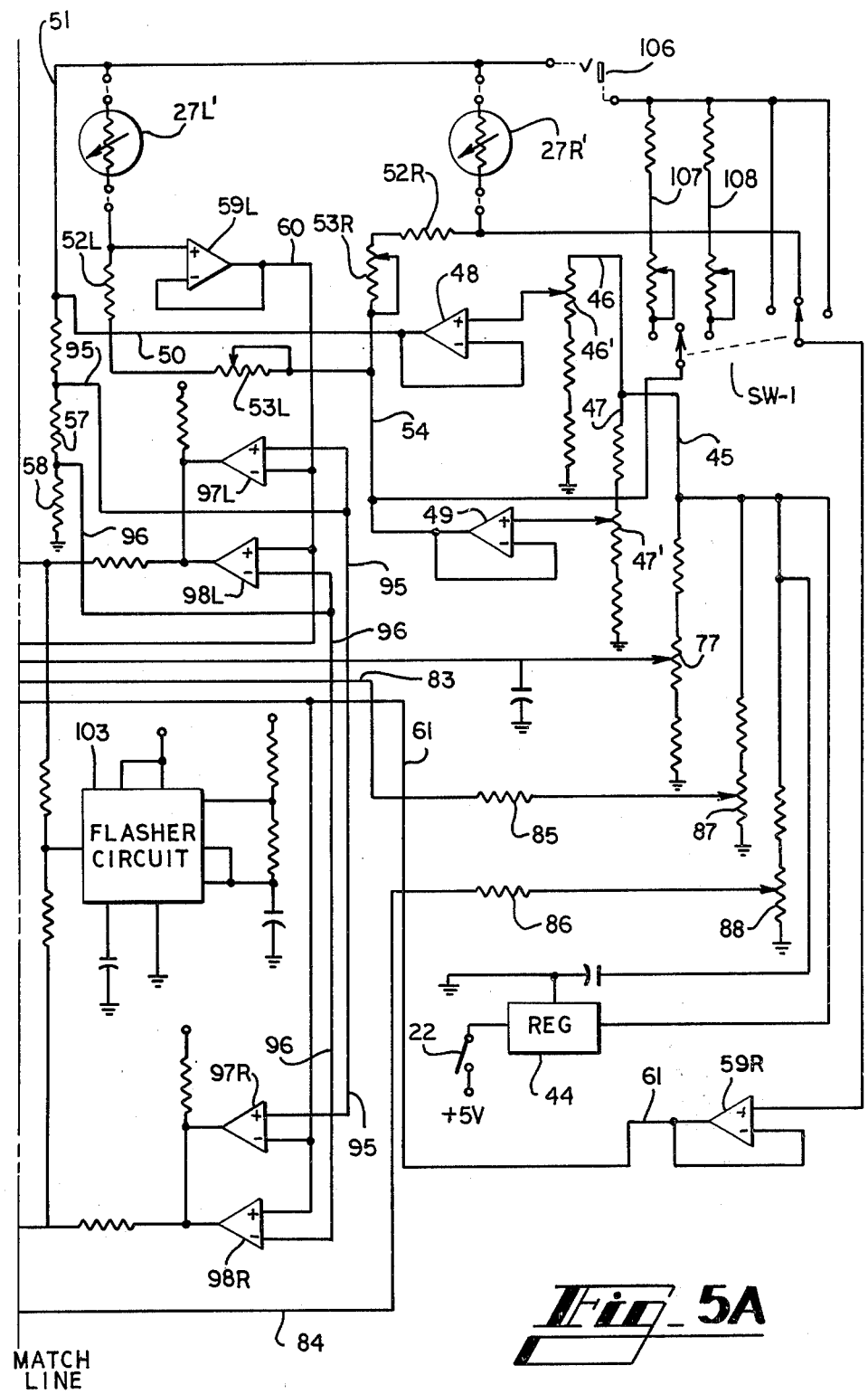
FIGS. 5A and 5B combined are a schematic diagram showing circuit details of the disclosed embodiment.

Turning first to FIG. 1, there is shown generally at 10 a bipolar temperature indicator according to the disclosed embodiment of the present invention, and including a relatively flat rectangular housing 11, having a back end 13 from which the handle 12 extends downwardly. Extending upwardly from the front end 14 of the housing 11 is a pair of temperature sensing assemblies 15L and 15R, which are described below in greater detail.

A control member 16, which is mechanically interconnected with the temperature sensing assemblies 15A and 15B to adjust the lateral position between those assemblies, extends outwardly from the top surface 17 of the housing 11. Also positioned on the top surface 17 are the temperature indicating display panels 20L and 20R, which are connected by way of circuitry disclosed below to provide a digital readout of the skin temperature sensed by the respective temperature sensing assemblies 15L and 15R.

A control switch 21, which controls operation of the temperature indicating displays in a manner discussed below, is located in the top 17 of the housing adjacent the back end 13. Another control switch 22 for controlling the overall operation of the bipolar temperature indicator 10 is located near the inner end of the handle 12 on its underside, for convenient manual operation by a person grasping the handle.

Each of the temperature sensing assemblies 15L and 15R includes a mounting head 26, and a temperature sensing element 27 is disposed in outwardly-facing relation on the forward surface of each mounting head. The mounting head 26 in each temperature sensing apparatus is flanked by a pair of rollers 28, with each pair of rollers being rotatably supported on the respective mounting head for free rotation as the bipolar temperature indicator 10 is moved along a person's body. The diameter and mounting position of the rollers 28, relative to the temperature sensing elements 27, is selected so that the rollers allow the temperature sensing assemblies 15L and 15R to traverse along the skin surface with the temperature sensing element 27 in temperature-sensing operative relation with the skin surface of the body.

One of the rollers, such as the roller designated 28' in the sensing assembly 15R, is coupled with a motion-responsive device 31, FIG. 4, which generates signals in response to rotation of the roller so as to indicate the distance traversed by the bipolar temperature indicator 10 along a person's skin. The motion responsive device 31 may be any device which produces signals corresponding to the amount of roller rotation, without materially impeding rotation of the roller 28. The motion responsive device 31 as seen in FIG. 3 includes a source of electromagnetic radiation such as a photoemitter 31a, directing a radiation beam 32 toward the exterior surface of the roller 28, and a radiation-responsive device such as the photoreceptor 31b, positioned to receive the radiation beam 33 reflected from the roller's periphery. The peripheral surface of the roller 28' is preferably provided with alternating light-reflecting and light-absorbing bands as best seen in FIG. 1, so that the beam 33 of radiation reflected from the roller is alternately "chopped" or interrupted as the roller rotates. The output signal from the photoreceptor 31b thus consists of a series of square-wave pulses which can be amplified and then applied to a distance-measuring responsive device such as a chart recorder, in a manner known to those skilled in the art. Alternatively, the motion-responsive device 31 may be a Hall-effect device which is actuated by a suitable magnetic rotor disposed internally within the roller 28'.

The mounting head 26 of each temperature sensing probe assembly 15L and 15R is pivotably mounted within a shroud 34 by a pivot pin 35, so that each of the mounting head is free to adjust to minor variations in the contour of the body surface as the bipolar temperature indicator 10 traverses that surface. The shroud 34 of each probe assembly is, in turn, pivotable about a vertical axis disposed inwardly of the pivots 34 (and concealed within the housing 11 in FIG. 1) so that the nominal spacing between the two probe assemblies can be varied. The pivotable mounting of the probe assemblies 15L and 15R constitutes a primary and controllable positioning of the probe assemblies, and is adjustable by operation of the control member 16 to select the desired spacing between the bipolar probe assemblies; the pivotable mounting of the mounting heads 26 about the pivots 35 constitutes a secondary pivot which allows each individual probe assembly to float, so as to accommodate minor variations in body contour.

A suitable linkage interconnecting the two probe assemblies 15L and 15R with the control member 16, is shown in FIG. 3, looking upwardly at the top interior of the housing 11 wherein each of the shrouds 34 is seen to be mounted for pivotable movement about the shaft 36 extending into an opening at the inner end of the shroud. A separate link 37 extends from each shroud 34 to a pivotable connection with the wheel 38 coupled to the control knob 16. A pin 39 extends perpendicular to the outer end of each link 37 and is pivotably received in an opening 40 in the corresponding shroud 34, located a distance in front of the pivot shaft 36 for the shroud. Rotating the control knob 16 in either direction concurrently extends or retracts both links 37, so that rotating the control member in a selected direction either enlarges or diminishes the spacing between the probe assemblies. A spring-loaded detent pin 41 selectively engages the recesses 42 on the periphery of the wheel 38 to provide a number of discrete position adjustments.

The probe assemblies 15L and 15R are symmetrically disposed along the width of the housing 11, and the handle 12 of the bilateral temperature indicator 10 joins the housing along a line which substantially bisects the spacing between the probe assemblies. In operating the instrument, accordingly, the user grasps the handle 12 and traverses the instrument along a patient's back which the handle 12 is visually aligned with the spinal column of the patient, thereby causing each of the probe assemblies 15L and 15R (at the spacing selected by the control knob 16) to be bilaterally disposed equidistant of the spinal column).

Figure 5B:
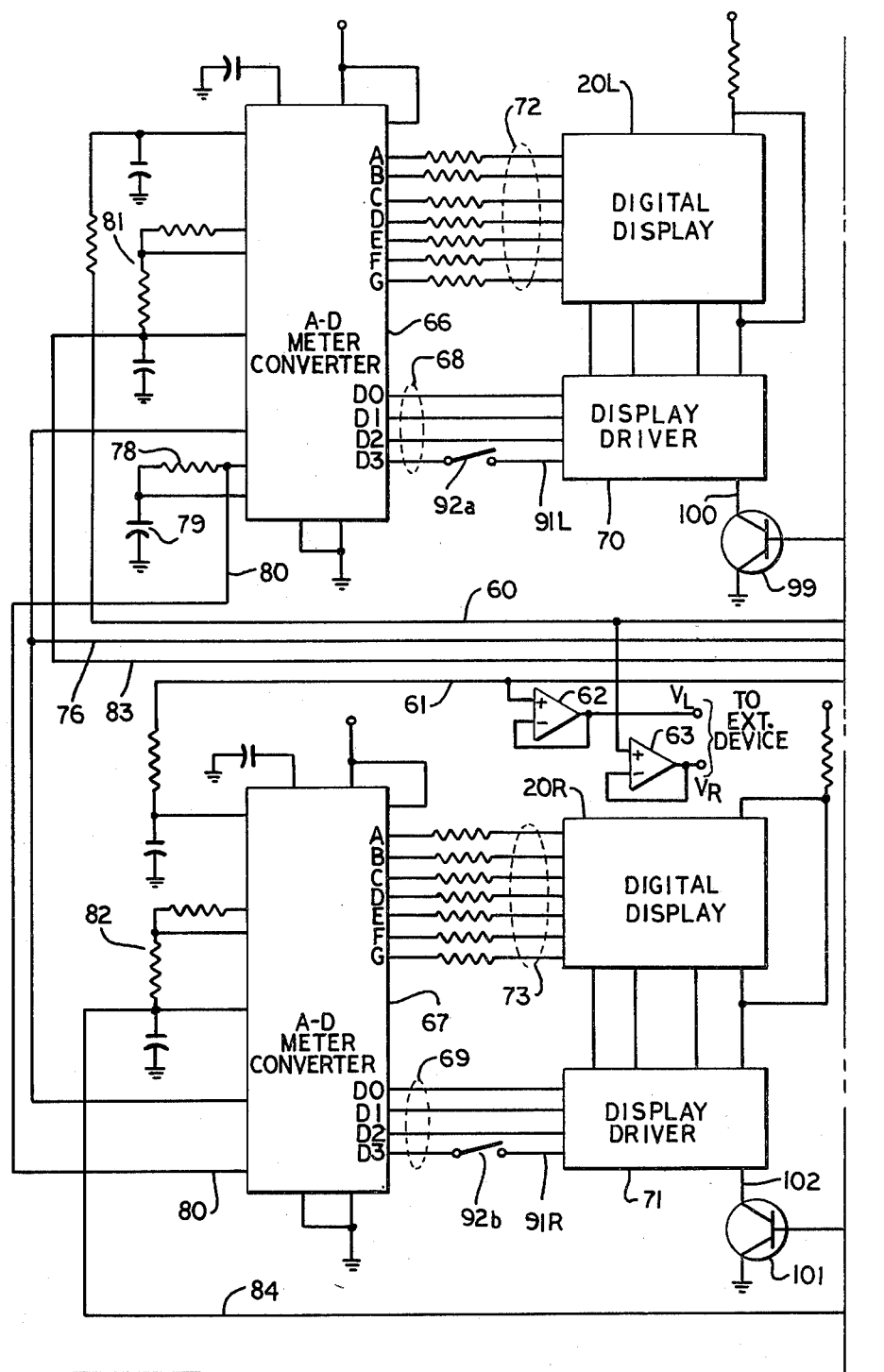

Turning next to FIGS. 5A and 5B and the schematic diagram shown therein, the nature and operation of the temperature sensing and display circuitry for the bipolar temperature indicator 10 are discussed.

The temperature sensing elements 27 of the two probe assemblies 15L and 15R comprise sensors 27L' and 27R' provided by thermistors, thermally sensitive resistors whose primary function is to change electrical resistance with a change in temperature of the thermistor. The sensors 27L' and 27R' should be capable of an acceptable degree of linearity over the desired range of skin temperatures, e.g., accuracy to within about 0.3° F. over a temperature range of 75°–105° F., and the sensors should have a sufficiently low thermal inertia to permit accurate detection of variations in skin temperature while being moved along the skin surface. In an actual embodiment of the present bipolar temperature indicator, a thick film flake thermistor sensor assembly known as a Thinistor and supplied by Victory Engineering Corporation of Springfield, N.J. as part number SFN59 satisfies the foregoing desirable operating characteristics. Further details of the temperature sensing elements are discussed below.

Each of the temperature sensors 27L' and 27R' is connected in series with a separate voltage divider network containing resistances selected to linearize, as closely as possible, the resistance-temperature operating characteristic of the thermistor device across the desired operating temperature range, in a manner known to those skilled in the art. The voltage divider networks include a voltage regulator 44 connected to a suitable DC voltage source such as a rechargeable battery pack contained within the handle 12 of the housing. Regulated voltage appears on the line 45 and is supplied to a number of divided networks, including the voltage dividers 46 and 47 which include potentiometers 46' and 47' in series with a pair of fixed resistances. The potentiometers 46' and 47' associated with the respective divider networks each supply an input voltage to a corresponding pair of operational amplifiers 48 and 49, which operate to buffer the voltages selected from the potentiometers. The buffered output voltage from the operational amplifier 48 is supplied along lines 50 and 51 to one side of each temperature sensor 27L' and 27R', and provides a "high" voltage for those sensors. The other side of each sensor is connected through fixed resistances 52L, 52R and variable resistances 53L, 53R, respectively to line 54, which receives the buffered voltage from operational amplifier 49 and comprises the "low" voltage supplied to the pair of temperature sensing elements. It will be seen that the buffered voltage on line 50 also passes through a voltage divider network including resistances 57 and 58, for a purpose described below.

The amount of current flowing in each of the circuits including the respective temperature sensors 27L' and 27R' is determind by the temperature-responsive resistance of each sensing element, and the corresponding voltage across each of the resistances 52L and 52R is supplied to a separate operational amplifier 59L and 59R for buffering. The three-position two-section ganged selector switch SW-1 is assumed to be in its depicted center position at this time. The buffered output voltages from the operational amplifiers 59L and 59R appear on lines 60 and 61 as $V_L$ and $V_R$, respectively, and are analog voltages corresponding to the skin temperatures separately measured by each of the temperature sensors 27L' and 27R'. Those analog voltages $V_L$ and $V_R$ are supplied to separate panel meter circuits shown shown in FIG. 5B for digitizing and driving a digital display, as described below. The voltages $V_L$ and $V_R$ are also made available to operate an external device, such as a chart recorder or the like, preferably by passing the voltages through additional buffering operational amplifiers 62 and 63 and thence to a suitable output connector 64, which may be located in the outer end of the handle 12 (FIG. 2) associated with the bipolar temperature indicator.

Turning next to FIG. 5B, the temperature-derived voltages are supplied along the lines 60 and 61 to provide inputs for the separate panel meter display converters 66 and 67, which are standard elements operating to convert the analog voltage input to digital output signals necessary to drive a digital display. Each of the panel meter converters 66 and 67 supplies digital signals corresponding to four-digit temperature information, including tenths of a degree, along four lines collectively denoted 68 and 69, respectively, to a display driver circuit 70 and 71, respectively. The display driver circuits are connected to drive the digits of the four-digit temperature display panels 20L and 20R, also seen in FIG. 1. Each of the digital display panels 20L and 20R also receives display driving power from the respective meter converters 66 and 67 through respective lines collectively designated at 72 and 73, and containing current-limiting resistors.

The panel meter converters 66 and 67 are connected to receive a common reference voltage on line 76, which is connected to a potentiometer 77 forming part of another voltage divider supplied with the regulated voltage along the line 45. The resistance 78 and capacitance 79 associated with panel meter converter 66 form part of the clock operating circuit for that converter, and the clock signal is supplied on line 80 to provide clock input signals to the other panel meter converter 67. The integrator circuits indicated at 81 and 82, required for the operation of each meter chip 66 and 67, are separately supplied with operating voltages on the lines 83 and 84, through current-limiting resistors 85 and 86 (FIG. 5A) respectively connected to the potentiometers 87 and 88 connected in separate voltage divider circuits across the regulated voltage on line 45. The zero offsets of the converter circuits 66 and 67 are adjusted by the potentiometers 87 and 88.

The tenths-digit line 91L and 91R, in each set of digit lines 68 going to the display drivers 70 and 71, passes through normally-closed kill switches 92a and 92b, and those kill switches are ganged together to be momentarily opened whenever the switch 21 (FIG. 1) is actuated. The two digital displays 20L and 20R can thus be controlled to omit the tenths digit, at the command of the user.

Because the temperature sensors 27L' and 27R' are operating in circuits selected to provide substantial linearity over a preselected range of skin temperatures, it is desirable to know when a skin temperature signal from either sensor falls outside that temperature range. Signals corresponding to the upper and lower limits of the temperature range are defined by the previously-identified voltage divider resistors 57 and 58, connected to the "high" buffered voltage on line 50. The values of those resistors are selected to provide voltages on the lines 95 and 96 corresponding to temperatures slightly above and slightly below, respectively, the selected upper and lower limits of the preselected range of skin temperatures to be measured with the instrument. The upper-end voltage on line 95 provides an input to the upper-limit comparators 97L and 97R, and the lower-limit voltage on line 96 provides an input for the comparators 98L and 98R. Each of the left-probe comparators 97L and 98L is connected to receive the buffered analog voltage on the line 60, and the right probe comparators 97R and 98R likewise are connected to receive the analog temperature voltage on the line 61. The outputs of the two left-probe comparators 97L and 98L are connected to a transistor 99 (FIG. 5B) in series with the ground connection 100 of the display driver 70 for the left display panel 20L, and the outputs of the comparators 97R and 98R are similarly connected to drive the transistor 101 in series with the ground line 102 of the display driver 71 for the right display panel 20R. The ground-switching transistors 99 and 101 are connected in parallel to receive control signals from the flasher circuit 103, which operates to provide an on-off signal at a visually-detectable rate of, for example, about five to ten hertz.

The temperature-responsive signals provided by each of the sensors 27L' and 27R' are constantly compared with the voltages on lines 95 and 96, corresponding to the preselected maximum and minimum voltages in the temperature measuring range. Whenever one of the measured voltages fall either above or below the range, as determined by an output signal from the appropriate comparator 97L, 98L or 97R, 98R, the transistor 99 or 101 is driven to turn on and off periodically at a rate determined by the flasher circuit 103, thus causing the indication appearing on the corresponding digital display 20L or 20R to blink at a rate determined by the flasher circuit. The person using the bipolar temperature indicator thus is immediately made aware that the displayed temperature on either (or both) displays falls outside a predetermined range of linearity. At the same time, it will be appreciated that the flashing display continues to indicate the measured temperature.

It may be desired to use the temperature measuring and indicating circuits of the foregoing bipolar temperature indicator in connection with an external temperature probe, such as an oral thermometer probe or the like. The external input connector 106 (FIG. 5A) is provided for that purpose; that connector may be mounted on the underside of the housing 11, at a location not shown in FIG. 1 or 2. Whenever the selector switch SW-1, which is shown in center position for temperature measurement using the internal temperature sensors 27L' and 27R', is moved to either its left or right positions, the connector 106 replaces the sensor 27R' as a source of input signals to the operational amplifier 59R. A suitable external temperature sensing probe plugged into the connector 106 is thus placed in series with one or the other of the two voltage divider circuits 107 or 108, depending on the position of selector switch SW-1, and the input of operational amplifier 59R is connected across that selected divider circuit. The potentiometers in the external-probe voltage divider circuits 107 and 108 are preset to calibrate those circuits to the particular type of external probe, and it will be appreciated that two such voltage divider circuits are present along with corresponding selector switch positions so that either of two types of external probes having different temperature-resistance characteristics may be selectably used with the present instrument.

It will be appreciated by those skilled in the art that the various potentiometers shown in FIGS. 5A and 5B are all located within the housing 11 of the bipolar temperature indicator, and are initially preset during manufacture to calibrate the instrument. The potentiometers 46' and 47' are set to provide the upper and lower voltage reference points as discussed above, and the potentiometers 53L and 53R are adjusted to fine-tune the respective temperature sensor circuits for the exact properties of the sensor actually used in each circuit. The remaining potentiometers likewise permit calibration at the time of manufacture, to accommodate minor differences in resistances and other values of the individual circuit elements.

Details of a typical temperature sensing probe 27 are shown in FIG. 6. The probe includes a post 112 made of a relatively poor thermal heat sink such as wood or the like, mounted in and extending outwardly from the mounting head 26. The outer end of the post 112 is covered by a cap 113 made of a good thermal conductor such as copper or the like. The cap 113 has a smooth face 114 for contacting the skin of a person's body, and has a cylindrical flange 115 extending over the outer end of the post 112 and affixed thereto by cementing. The thickness of the cap face 114 may be on the order of 0.001 inch. The inside surface of the face 114 is spaced outwardly from the end of the post 112, and the temperature sensing thermistor 116 (corresponding to either of the sensors 27L' or 27R' in FIG. 5A) is secured to that inside surface by means of epoxy cement or the like which electrically insulates the thermistor from the electrically-conductive cap 113. Leads 118 extend through the post 112 to interconnect the thermistor with electrical circuitry shown in FIG. 5A.

The use of a relatively thin cap 113 reduces the thermal lag of the probe 27, and permits the probe to be moved along a skin surface while producing accurate readings on the move. The insulative supporting post 112 and the air space 117 between the post and the surface 114 also reduce the thermal lag of the probe.

The foregoing discloses a compact, hand-held bipolar temperature indicator for providing a digital indication of skin temperature at bilateral points along the spinal column, or at any other desired location on the skin of a person or other living organism. The temperature signals, in addition to appearing on the digital displays, can be supplied to an external device such as a dual-channel strip chart recorder, and the paper feed of the strip chart can be driven by signals from the motion-responsive device 31, FIG. 4. In that manner, a strip chart can readily be generated for a particular patient, showing the instantaneous measured skin temperature at bilateral locations along the spinal column, plotted along a length of strip chart that corresponds in length to the distance traversed by the bipolar temperature indicator 10. That length of paper can then be removed from the strip chart recorder and positioned along the patient's spinal column, so that indicated skin temperature anomalies recorded on the chart paper can be directly translated into corresponding locations along the spinal column for further examination or adjustment.

It should be understood that the foregoing relates only to a preferred embodiment of the present invention, and that changes and modifications may be made therein without departing from the spirit and the scope of the present invention as defined in the following claims.

We claim:
1. Hand-held apparatus for measuring the skin temperature of a living organism, comprising:
means defining a housing having a first portion configured to be manually grasped and having a second portion configured for disposition in proximity to the skin surface of a living organism;
a pair of temperature responsive means mounted in predetermined mutually spaced apart relation on said second portion, each of said temperature responsive means being operative to produce an electrical signal in response to skin temperature adjacent the temperature responsive means;
circuit means carried by said housing means and selectably operative in response to said electrical signals from each of said temperature responsive means to provide a first temperature signal corresponding to the skin temperature served by said first temperature responsive means, and to provide a second temperature signal corresponding to the skin temperature served by said second temperature responsive means;
a pair of display means carried by said housing means and respectively operative in response to said first and second temperature signals to provide a simultaneous visual indication of the skin temperatures observed by said pair of temperature responsive means;
said second portion of said housing means being configured to be traversed along the skin surface while said skin temperature sensing means remain in temperature sensing contact with the skin surface; and
means carried by said housing means and responsive to movement along the skin surface to produce a signal indicating the distance traveled by said skin temperature sensing means as said housing means is traversed along the skin surface.

2. Skin temperature measuring apparatus as in claim 1, wherein:
said pair of skin temperature responsive means is mounted in said spaced apart relation along a predetermined sensing axis and further comprising
adjustable means mounting each of said skin temperature responsive means for equal but opposite selectable positioning along said axis with respect to a reference location on said axis, so that the spacing between each of said skin temperature sensing means relative to said reference location is simultaneously adjustable by said adjustable means.

3. Skin temperature measuring apparatus as in claim 1, further comprising:

means operative to provide lower and upper limit signals corresponding to predetermined minimum and maximum temperatures so as to define a range of temperatures within which said circuit means is responsive to said electrical signals to provide said first and second temperature signals with predetermined substantial linearity; and means operative in response to said first and second temperature signals and said limit signals to provide a characteristic visual indication in said display means whenever the measured skin temperature denoted by a temperature signal falls outside said predetermined linear range of temperatures.

4. Skin temperature apparatus as in claim 1, wherein each of said temperature responsive means comprises:

a mounting post having poor heat absorbent characteristics and extending outwardly from said housing means;

a metallic cap mounted on the outwardly extending end of said post, said cap having a smooth skin contacting outer surface and an inner surface; and a temperature responsive element mounted on said inner surface to provide said electrical signal in response to the temperature of said inner surface, so that the temperature of skin contacted by said outer surface is rapidly transferred through the cap to the temperature responsive element without heat loss into said mounting post.

5. Apparatus as in claim 4, wherein:

said inner surface is disposed in spaced apart relation to define an air space between the end of said post and said temperature responsive element, said air space reducing unwanted heat transfer between the inner surface and the post end so as to reduce the thermal lag of said temperature responsive means.

6. Skin temperature apparatus as in claim 1, wherein each of said temperature responsive means comprises:

mounting means having poor heat conductance and housing a portion extending outwardly from said housing;

a member having good heat conductance and mounted on said outwardly extending portion so as to minimize heat transfer between said member and said mounting means, said member having a smooth outer surface for contacting the skin and having an inner surface; and temperature responsive means operatively associated with said inner surface to provide said electrical signal in response to the temperature of said inner surface, so that the temperature of skin contacted by said outer surface is rapidly transferred through the member to the temperatures responsive means without loss into said mounting means.

7. Apparatus as in claim 6, wherein:

said inner surface is spaced apart from said mounting means to define an air space between the inner surface and said outwardly extending portion, said air space reducing unwanted heat transfer between the inner surface and the outwardly extending portion so as to reduce thermal lag of said temperature responsive means.

8. Hand-held apparatus for measuring the skin temperature of a living organism, comprising:

means defining a housing having a first portion configured to be manually grasped and having a second portion configured for disposition in proximity to the skin surface of a living organism;

a pair of temperature responsive means mounted in predetermined mutually spaced apart relation on said second portion, each of said temperature responsive means being operative to produce an electrical signal in response to skin temperature adjacent the temperature responsive means;

circuit means carried by said housing means and selectably operative in response to said electrical signals from each of said temperature responsive means to provide a first temperature signal corresponding to the skin temperature served by said first temperature responsive means, and to provide a second temperature signal corresponding to the skin temperature served by said second temperature responsive means;

a pair of display means carried by said housing means and respectively operative in response to said first and second temperature signals to provide a simultaneous visual indication of the skin temperatures observed by said pair of temperature responsive means;

means operative to provide limit signals corresponding to predetermined minimum and maximum temperatures so as to define a range of temperatures therebetween; and means operative in response to said first and second temperature signals and said limit signals to provide a characteristic visual indication in said display means whenever the measured skin temperature denoted by a temperature signal falls outside said range of temperatures;

said means operative to provide limit signals comprising a first circuit operative to provide a reference voltage to each of said temperature responsive means;

said temperature signals comprise voltages separately corresponding to measured temperatures;

a second circuit connected to receive said reference voltage and operative to provide first and second temperature limit voltages as functions of said reference voltage; and signal comparison means separately responsive to each of said measured temperature voltages, and to both of said temperature limit voltages, and operative to provide a periodic signal to a selected said visual display means whenever the temperature voltage operating that display means exceeds either of said first or second temperature limit voltages.

9. Apparatus as in claim 8, wherein said display means comprises digital display means; and said means to provide a characteristic visual indication is operative to blink said visual display means at a rate determined by said periodic signal.

10. Hand-held apparatus for measuring the skin temperature of a living organism, comprising:

means defining a housing having a first portion configured for disposition in proximity to the skin surface of a living organism;

a pair of temperature responsive means mounted in predetermined mutually spaced apart relation on said second portion, each of said temperature responsive means being operative to produce an electrical signal in response to skin temperature adjacent the temperature responsive means;

circuit means carried by said housing means and selectably operative in response to said electrical signals from each of said temperature responsive means to provide a first temperature signal corresponding to the skin temperature served by said first temperature responsive means, and to provide a second temperature signal corresponding to the skin temperature served by said second temperature responsive means;
a pair of display means carried by said housing means and respectively operative in response to said first and second temperature signals to provide a simultaneous visual indication of the skin temperatures observed by said pair of temperature responsive means;
said display means comprising a pair of digital display means operative to indicate temperature to the nearest tenth of a degree; and
means associated with said display means and selectably operative to simultaneously cancel only the tenths indication of both of said digital display means, so that said digital display means selectably indicate the skin temperatures either to the degree or to the tenth of a degree.

* * * * *